United States Patent [19]
Robicsek

[11] Patent Number: 5,139,515
[45] Date of Patent: Aug. 18, 1992

[54] ASCENDING AORTIC PROSTHESIS

[76] Inventor: Francis Robicsek, 1960 Randolph Rd., Charlotte, N.C. 28207-1199

[21] Appl. No.: 567,830
[22] Filed: Aug. 15, 1990
[51] Int. Cl.[5] .............................................. A61F 2/06
[52] U.S. Cl. .......................................... 623/1; 623/2
[58] Field of Search ..................... 623/1, 2, 900, 11, 12

[56] References Cited
U.S. PATENT DOCUMENTS
4,350,492 9/1982 Wright et al. ......................... 623/1

Primary Examiner—David Isabella
Assistant Examiner—Gina M. Gualtieri
Attorney, Agent, or Firm—Shefte, Pinckney & Sawyer

[57] ABSTRACT

An ascending aortic prothesis has a root wall portion with annularly spaced bulges simulating the sinuses of Valsalva to provide a more natural functioning of the aortic valve following surgery to implant such prothesis in comparison to conventional aortic protheses which are of uniform tubular diameter.

2 Claims, 3 Drawing Sheets

ASCENDING AORTIC PROSTHESIS

BACKGROUND OF THE INVENTION

Three out-pouchings of the wall of the aortic root corresponding with the three leaflets of the aortic valve has been described by the Italian anatomist, Antonio Valsalva, in the fifteenth century. Animal and human physiologic studies indicate that these out-pouchings, i.e. the sinuses of Valsalva, may have favorable influence upon the function of the aortic valve. Studies have been conducted, both in ancient and modern times, which show that when the heart ejects blood, flow recoils at the edges of the aortic valve and exerts some degree of pressure on the lateral walls of the membranous aortic valve. As a result of this process the aortic valve begins to close before the cardiac contraction terminates and the disappearance of systolic gradient between the left ventricle and the aorta causes only the completion of closure of the aortic valve but not the initiation of the same.

Aortic valve prostheses (with or without an artificial aortic valve inside) uniformly disregard this physiologic phenomenon and aortic prostheses manufactured from sympatic tubes such as Dacron, of woven or knitted variety, which are made of "straight" tubes of constant diameters throughout, without such "out-pouchings," disregard the physiological principle of normal aortic valve function.

SUMMARY OF THE INVENTION

It is accordingly an object of the present invention to provide vascular prostheses to be applied in the replacement of the human ascending aorta which are configured upon physiological principles and which resemble the sinuses of Valsalva. Such prostheses could be produced without a valve for cases in which the person's normal aortic valve is left in loco or with a built-in bioprosthetic or mechanical valve prosthesis. Such a prosthesis is expected to function physiologically better and to provide a more effective valve closure, i.e. in proper time and with less regurgitation.

DESCRIPTION OF THE PREFERRED EMBODIMENT

Figure 1:
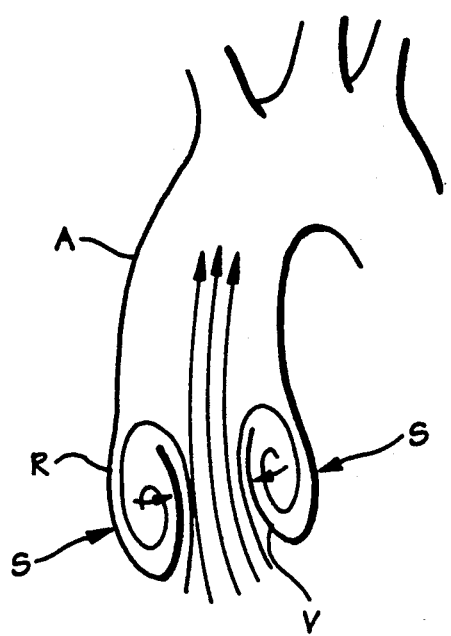
FIG. 1 is a schematic cross-sectional view of the aorta of the human body, showing the aortic root and aortic valve.
Figure 2:
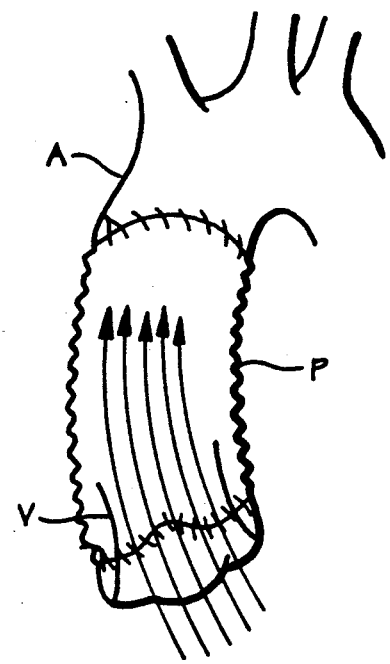
FIG. 2 is a similar cross-sectional view of the aorta with a conventional vascular prosthesis.
Figure 3:
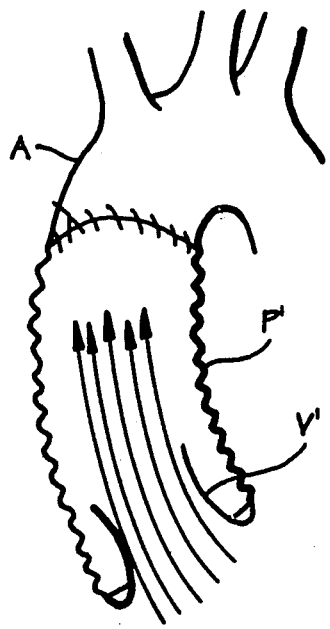
FIG. 3 is another similar cross-sectional view of the aorta with a conventional vascular prosthesis of the type having a bioprosthetic valve prosthesis.
Figure 4:
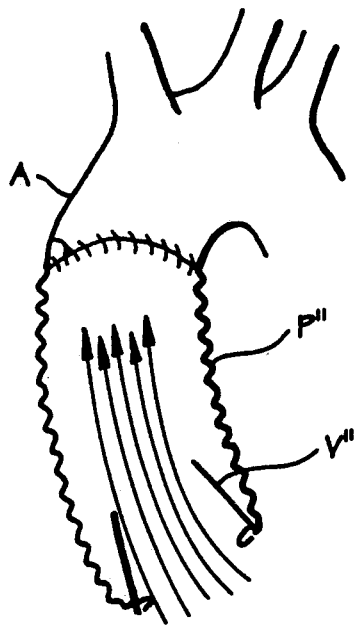
FIG. 4 is another similar cross-sectional view of the aorta with a conventional vascular prosthesis of the type having a mechanical valve prosthesis.

FIGS. 1-4 basically illustrate the known state of the art. FIG. 1 illustrates schematically the human aorta A wherein the wall of the aortic root R is formed with annularly spaced out-pouchings as indicated at S, which as described above are commonly referred to as the sinuses of Valsalva. The aortic valve is indicated at V. FIGS. 2-4 illustrate conventional aortic prostheses which as described above are basically of a tubular form having a substantially constant diameter throughout the length of the prosthetic tube. The prosthesis P of FIG. 2 is not equipped with a built-in artificial aortic valve for use in situations wherein the surgical patient's normal aortic valve is to be left in loco. In contrast, the prostheses P',P" of FIGS. 3 and 4, respectively, are equipped with built-in artificial aortic valves V',V", the valve V' being of the bioprosthetic type and the valve V" being of the mechanical valve type.

Figure 5:
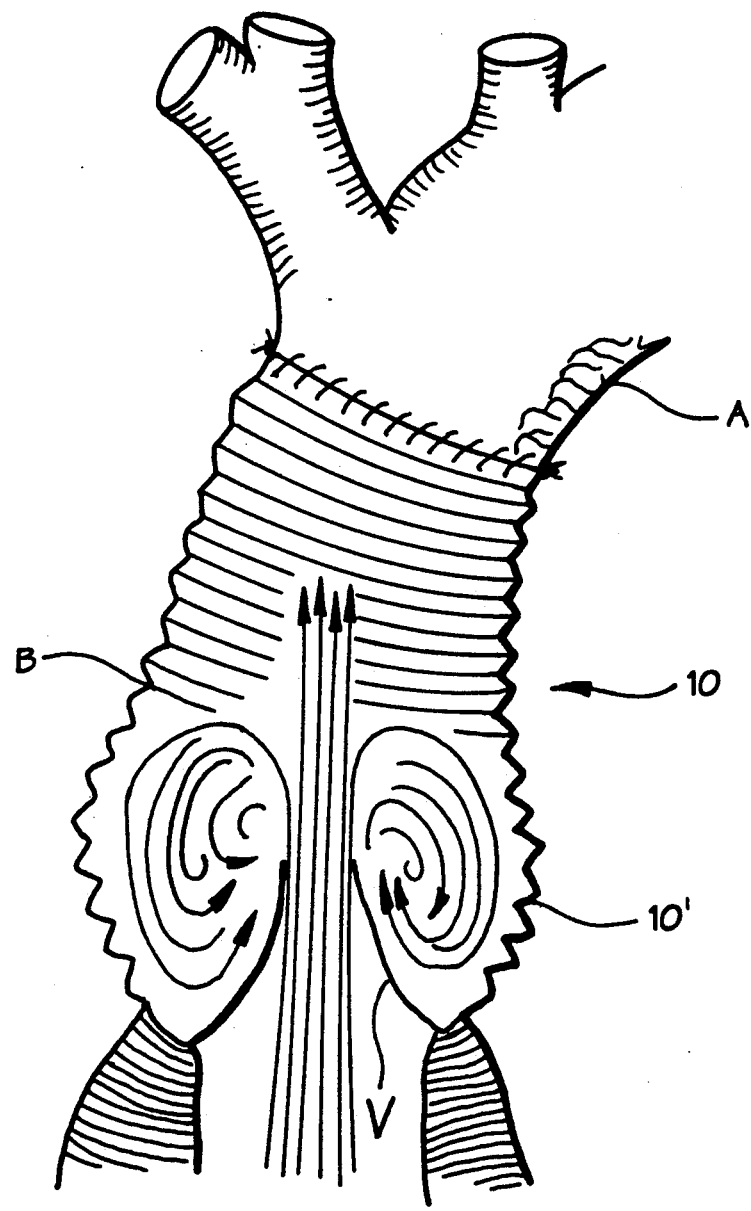
FIG. 5 and 6 are cross-sectional views of the aorta with an ascending aortic vascular prosthesis according to the preferred embodiment of the present invention.
Figure 6:
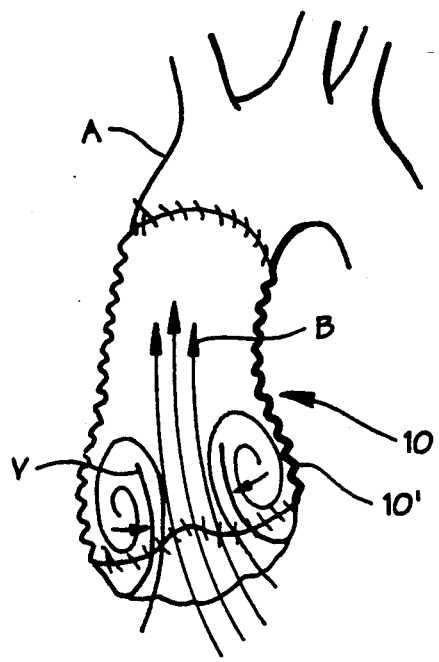
Figure 7:
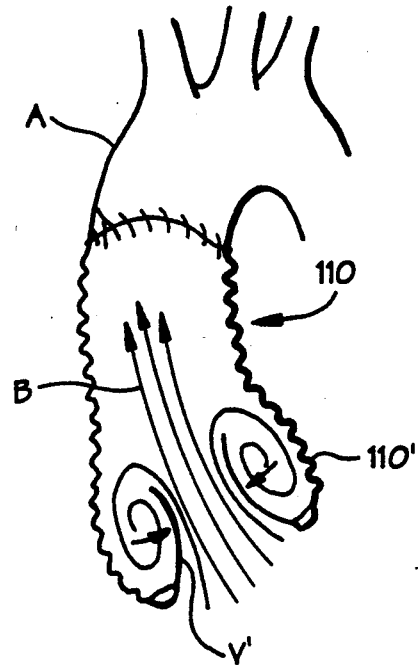
FIG. 7 is another cross-sectional view of the aorta with an ascending aortic vascular prosthesis according to another embodiment of the present invention.
Figure 8:
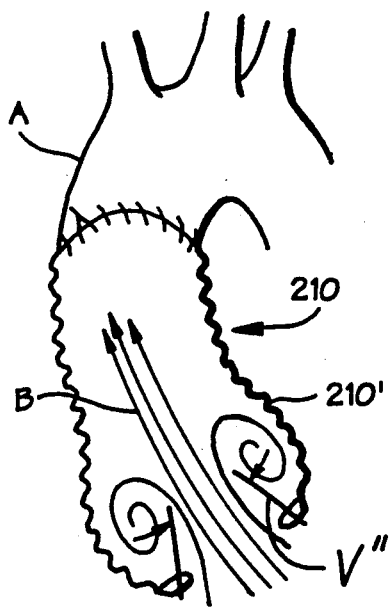
FIG. 8 is another cross-sectional view of the aorta with an ascending aortic vascular prosthesis according to a third embodiment of the present invention.

The aortic prosthesis according to the present invention is shown in FIGS. 5 and 6 generally at 10. Basically, the prosthesis 10 is of a tubular construction formed by an annular wall of a crimped material similar to that of conventional prostheses shown in FIGS. 2-4, but the annular wall of the prosthesis 10 at its root end 10' is formed with annularly spaced bulges so as to have a greater effective diameter than the remaining lengthwise extent of the prosthesis 10 in at least generally similar correspondence to the natural biological configuration of the sinuses of Valsalva in the human aorta of FIG. 1. The prosthesis 10 of FIGS. 5 and 6 is not equipped with an artificial aortic valve for use in surgical procedures wherein the patient's normal aortic valve V is not removed. FIG. 7 illustrates an alternative embodiment of the aortic prosthesis of the present invention, generally indicated at 110, wherein a bioprosthetic valve prosthesis V' is affixed at the terminal end of the bulged root wall portion 110' of the prosthesis 110. Similarly, another embodiment of the present aortic prosthesis is indicated at 210 in FIG. 8 with a mechanical valve prosthesis V" affixed to the annular root wall portion 210' of the prosthesis 210.

In each of FIGS. 5-8, blood flow is indicated by the directional arrows B. As shown, the annularly spaced bulges in the root wall portion 10',110',210' are expected to produce a recoiling turbulence in the lateral extent of the blood flow behind the aortic valve V,V',V" to exert a closing pressure thereon in a manner substantially similar to the sinuses of Valsalva in a natural biological aorta. As such, it is anticipated that the present prosthesis will function in a physiologically more effective and advantageous manner for valve closure in proper timing and with less regurgitation than is experienced with conventional prostheses.

It will therefore be readily understood by those persons skilled in the art that the present invention is susceptible of a broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

I claim:

1. An ascending aortic prosthesis for surgical implantation to replace a defective root section of the aorta, comprising a tubular body having a root portion at one end, the tubular body having an inner surface and an outer surface, the inner surface of the root portion having an annular region for disposition immediately above the aortic valve upon implantation, said annular region of the inner surface being of a partially concave shape and having a greater internal diameter than the remaining extent of the inner surface of the tubular body and including plural annularly-spaced radially outward bulges to simulate the sinuses of Valsalva of a natural biological aorta.

2. An ascending aortic prosthesis according to claim 1 and characterized further by an aortic valve prosthesis fixed to and disposed inwardly of the root portion below the annular region thereof.

* * * * *